United States Patent [19]
Peery et al.

[11] Patent Number: 5,206,024
[45] Date of Patent: Apr. 27, 1993

[54] DENSITY ELEMENT FOR RUMINAL DELIVERY DEVICE

[75] Inventors: John R. Peery, Palo ALto; James B. Eckenhoff, Los Altos, both of Calif.

[73] Assignee: Alza Corporation, Palo Alto, Calif.

[21] Appl. No.: 814,083

[22] Filed: Dec. 24, 1991

Related U.S. Application Data

[60] Continuation of Ser. No. 591,923, Oct. 2, 1990, abandoned, which is a division of Ser. No. 335,028, Apr. 7, 1989, abandoned.

[51] Int. Cl.$^5$ .............................................. A23K 1/18
[52] U.S. Cl. ..................................... 424/438; 424/473
[58] Field of Search ................................. 424/438, 473

[56] References Cited

U.S. PATENT DOCUMENTS

| | | | |
|---|---|---|---|
| 3,056,724 | 10/1962 | Marston | 424/438 |
| 3,616,758 | 11/1971 | Komarov | 102/92 |
| 3,844,285 | 10/1974 | Laby | 128/260 |
| 3,948,263 | 4/1976 | Drake, Jr. et al. | 128/260 |
| 4,218,255 | 8/1980 | Bajpai et al. | 106/45 |
| 4,381,780 | 5/1984 | Holloway | 604/892 |
| 4,449,981 | 5/1984 | Drake, Jr. et al. | 604/890 |
| 4,505,711 | 3/1985 | Lucas | 604/892 |
| 4,578,263 | 3/1986 | Whitehead | 424/15 |
| 4,595,583 | 6/1986 | Eckenhoff et al. | 424/15 |
| 4,612,186 | 9/1986 | Eckenhoff et al. | 424/15 |
| 4,623,345 | 11/1986 | Laby | 604/892 |
| 4,642,230 | 2/1987 | Whitehead et al. | 424/15 |
| 4,662,879 | 5/1987 | Drake et al. | 604/892 |
| 4,670,248 | 6/1987 | Schricker | 424/19 |
| 4,671,789 | 6/1987 | Laby | 604/59 |
| 4,675,174 | 6/1987 | Eckenhoff | 424/15 |
| 4,684,524 | 8/1987 | Eckenhoff et al. | 424/489 |
| 4,732,764 | 3/1988 | Hemingway | 424/438 |
| 4,765,837 | 9/1988 | Whitehead | 75/249 |

FOREIGN PATENT DOCUMENTS 59-83703 5/1984 Japan.

*Primary Examiner*—Thurman K. Page
*Assistant Examiner*—D. Gabrielle Phelan
*Attorney, Agent, or Firm*—Steven F. Stone; D. Byron Miller; Paul L. Sabatine

[57] ABSTRACT

A corrosion resistent density element for use in ruminal delivery devices which fragments upon contact with the blades in grinding machinery without damage to the blades. The density element has density of at least about 1.5 g/ml and a transverse rupture strength no greater than about 30,000 psi.

17 Claims, 1 Drawing Sheet

DENSITY ELEMENT FOR RUMINAL DELIVERY DEVICE

This application is a continuation of U.S. patent application Ser. No. 07/591,923, filed Oct. 2, 1990, now abandoned, division of U.S. patent Ser. No. 07/335,028, filed Apr. 7, 1989, now abandoned.

This invention relates to ruminal drug delivery devices. More particularly, this invention relates to density elements for said devices. Still more particularly, but without limitation thereto, this invention relates to fragmentable density elements and their manufacture.

CROSS-REFERENCE TO RELATED APPLICATIONS

This application is related to PCT application No. PCT/US90/01870 filed Apr. 5, 1990.

BACKGROUND OF THE INVENTION

Ruminant animals, including cattle, sheep, giraffe, deer, goats, bison and camels, and more particularly cattle and sheep, comprise an important group of animals that require periodic administration of medicines, nutrients and other biologically active agents (which are hereinafter referred to in their broadest sense as "drugs") for the treatment and alleviation of various conditions and for better health.

Ruminants have a complex three or four compartment stomach, with the rumen being the largest compartment. The rumen serves as an important location for receiving and absorbing medicines and nutrients into other compartments including the abomasum and the intestine.

There are numerous ruminal delivery devices known in the art which are capable of prolongedly releasing drugs. These devices are easily swallowed by the ruminant or otherwise introduced into the rumen and remain within the rumen for a long period of time without being regurgitated or otherwise. Typical devices are those disclosed in U.S. Pat. Nos. 4,595,583 and 4,612,186 incorporated herein by reference.

In order to insure that these devices remain in the rumen for a prolonged period of time a density element is often incorporated into the device. Typically, the density element is manufactured from a material such as iron or steel, iron shot, iron shot coated with iron oxide, magnesium alloy, copper oxide or mixtures of cobalt oxide and iron powder, and the like. Such density elements typically have sufficient density to bring the overall density of the delivery device to a level greater than the density of ruminal fluid (approximately 1 gm/ml) and preferably to an overall density of at least 2 gm/ml.

In animals such as cattle raised for slaughter the density element will often remain in the carcass after slaughter. The rumen and ruminal contents of animals still containing ruminal delivery devices, including their density elements, are typically processed by rendering plants. Rendering plants comprise a highly automated and continuous operation and though such machinery is typically equipped with magnetic retrieval systems, these systems are not always effective for removing the density elements. The rigid density elements have caused extensive and costly damage to grinder blades and equipment.

It is an object of this invention to provide a density element for a ruminal delivery device having a density sufficient to maintain the delivery device in the rumen of a living animal and also reproducibly fragment into harmless particles without damage to machinery when the density element contacts the blades in the cutting and grinding equipment of a rendering plant.

Another object of this invention is to provide a density element having a transverse rupture strength less than or equal to that of bovine or ovine bone.

A further object of this invention is to provide a corrosion resistent density element for use in a ruminal delivery device having a density sufficient to maintain the device in the rumen for a long period of time and a transverse rupture strength less than or equal to bone.

These and other objects are achieved according to the present invention.

According to an embodiment of this invention, a corrosion resistent metal powder is dry blended with a binder and compression molded into a density element which may thereafter be coated with a polymer film to increase the strength and corrosion resistance of the density element.

BRIEF DESCRIPTION OF THE DRAWINGS

In the drawings, which are not drawn to scale, but rather are set forth to illustrate the various embodiments of the invention and wherein like reference numerals designate like parts, the drawings are as follows.

DESCRIPTION OF THE INVENTION

This invention will be described with respect to ruminal delivery devices of the type shown in the Figures, but it is not limited to the specific devices disclosed. The ruminal delivery device designs illustrated herein are merely exemplary of devices known to the art and the density element of this invention can be manufactured in any configuration and be adapted to fit in a ruminal delivery device of any configuration.

Figure 1:
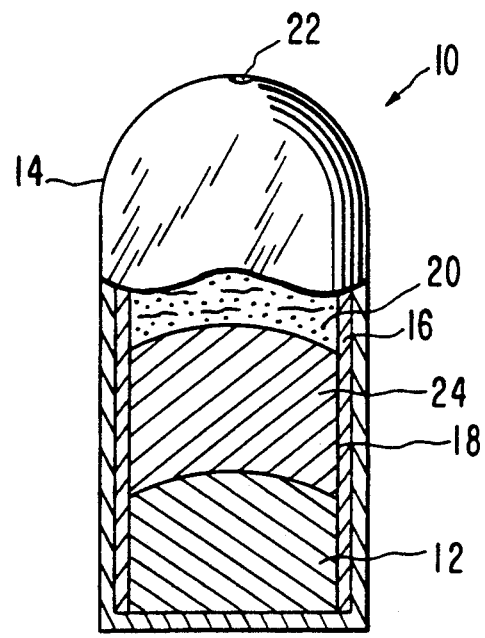
FIG. 1 is a partial cross sectional view of a ruminal delivery device having one embodiment of the density element of this invention.

FIG. 1 shows a device 10 having a density element 12 at the bottom of the device. The device would also be designed with a wall 14 which surrounds an internal capsule wall 16 and defines an internal lumen 18, which is partially shown in FIG. 1. The agent to be delivered can be dispersed throughout a thermo-responsive composition 20, which is delivered through a passageway 22 by pressure exerted upon said composition by an expandable member 24 which expands upon exposure of the device to ruminal fluid in a controlled manner as described in the aforementioned U.S. Pat. No. 4,595,583 and U.S. Pat. No. 4,612,186.

The density element 12 is flat bottomed so as to fit the contour of device 10. However it can have any shape desired and if the ruminal bolus device has a rounded bottom, the density element can likewise be shaped to conform to the curve.

Figure 2:
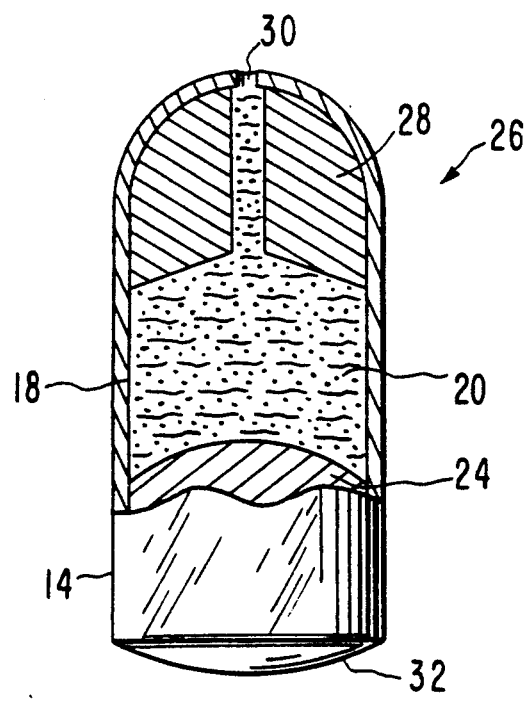
FIG. 2 is a partial cross-sectional view of a ruminal delivery device having another embodiment of the density element of this invention.

This invention also contemplates positioning the density element near the external passageway as is shown in the device 26 of FIG. 2. With the density element 28 so positioned, the passageway must extend through the density element 28 to the agent containing composition 20 contained within device 26. For purposes of illustration only, device 26 differs from device 10 by having only a single wall 14 and having a rounded bottom 32.

The density elements of this invention are characterized by having: a) a density sufficient to maintain the delivery device within the rumen of the animal to which it is administered; b) a corrosion resistance sufficient to prevent any significant loss in weight of said element in the rumen from administration to slaughter; and c) a transverse rupture strength that will allow the density element to reproducibly disintegrate into harmless particles or pieces without damage to cutting blades or other equipment that may contact the density element in the rendering process. Density elements according to this invention should have a density of from about 1.5–8 gm/ml or higher and preferably the density is within the range of about 2.2 to 7.6 g/ml. For ruminal bolus devices which are administered to cattle or sheep, it is preferred to use a density element such that there is a resulting overall density of the delivery device of about 3 g/ml. The density elements of this will also have a transverse rupture strength no greater than that of ovine or bovine bone which is approximately 30,000 psi.

Transverse rupture strength of a material is determined by standard ASTM tests in which test samples of a particular configuration are subjected to a standardized test. Because the density elements of this invention have a different configuration than that utilized in the standard tests, the transverse rupture strength of the elements of this invention may be determined by measuring the transverse rupture strength of standard shaped samples of a material manufactured under the same conditions as applied to the elements of this invention.

Transverse rupture strength of parts having other configurations such as the cylindrical parts of the Figures may also be determined indirectly form another parameter, radial crush strength. In a radial crush test the density element is crushed to yield between two parallel plates. Because radial crush strength is a geometry dependent property, an initial correlation between radial strength and transverse rupture strength must be made by tests on samples of the particular geometry having known transverse rupture strengths.

The density elements of this invention may be formed by sintering, partial sintering or molding of metal elements, preferably particles.

Sintering is a process of heating small particles to agglomerate them into bulk materials by establishing bonds between the particles. In order for sintering to occur, a bond must develop between the particles either through the formation of a liquid phase between the particles or by solid diffusion between the particles. In typical sintering processes of the prior art the part is sintered for a time and at a temperature sufficient to permit a weld bond to form between the particles. As a result, typical metal sintering process produce a metal product which exhibits strength properties approaching those of metals subjected to conventional metallurgical processes which involved melting of the metallic material. The sintering process of this invention, however, is conducted under conditions which prevent the formation of full weld bonds and thereby provides a product having a much lower transverse rupture strength than would be obtained by typical sintering procedures.

In the preferred embodiment of this invention, a density element is comprised of an agglomeration of dense particles, that will reproducibly fragment into component particles, smaller agglomerates or powder upon impact with grinding blades or typical forces encountered in rendering plants without damaging the equipment.

The density element of this invention can be manufactured by the different processes generally described above and can be formed of any dense, preferably metallic material, which would not react with the ruminal fluid in a manner that would interfere with its functioning as a density element. Iron, because of its density, cost and chemical and biological properties is preferred according to this invention.

The size of the metal powder affects the density and transverse rupture strength of the finished product and the preferred particle size is 100%<100 mesh and 85%<325 mesh. To reduce the transverse rupture strength of the end product, the metal powder can optionally be combined with silica powder or another suitable high density non-metallic or non-alloyable metallic filler material that will interfere with the formation of weld bonds between the metal particles. The filler material would have a particle size comparable to that of the metal powder and is preferably present in amounts of from 0–50% by volume. A small amount of a lubricant may also be added to the mixture to facilitate uniform compression as is known in the sintering art. Suitable lubricants include waxes and oils and may typically be present in amounts of about 0–5% by wt.

The addition of the filler decreases the transverse rupture strength of the density element and, since typical fillers are less dense than the metal, also the density. The particle size of both the filler material and the metal powder also have an effect on the strength and density of the finished item and can be varied to obtain the desired combination of density and transverse rupture strength. Generally, larger particle sizes of the metal and the filler will produce lower density end items. Generally, larger filler particles and smaller metal particles will produce lower transverse rupture strengths of the finished product.

The metal powder/filler particle mixture is compressed into the desired configuration and to approximately the desired density in a suitable die. The compression force should be at least sufficient to provide sufficient green strength to permit handling of the part in its green state which should be within the range of 1000–3000 psi and preferably about 1700–1800 psi. Typically the compression force required to achieve adequate green strength is within the range of 10–40 tons/in$^2$ and preferably about 30 tons/in$^2$.

Compression is followed by sintering in an inert atmosphere at a temperature below the standard sintering temperature used to achieve weld bond strength for the metal forming the density element. For iron, the preferred sintering temperatures according to this invention are in the range of about 1500°–2500° F.

Sintering may be followed by heat treatment in an oxidizing furnace. Heat treatment is normally done at temperatures ranging from 500°–1500° F. The resulting product has the added advantage of having an oxidized surface finish which is mildly corrosion resistant.

In another embodiment of this invention the desired strength and density are achieved by a molding process in which the dense particles are mixed with a binder, typically a wax, polymer or polymerizable material, and molded under heat and pressure to the desired geometry and approximate desired density. If the product is formed of an oxidizable metal it may then be heated to approximately 1000° F. in an oxygen-rich environment, to impart a stable oxide coating to the surface. The heat treatment also enhances the interparticle bonding without significantly increasing the product's strength.

According to this embodiment of the invention, the dense powder will correspond in characteristics to those described above and the wax, polymer or polymerizable will have a melting point low enough to permit it to flow around the dense particles to form a binding matrix at temperatures encountered in the molding process which are preferably limited to below 500° F. Suitable materials include, without limitation, hydrocarbon waxes, and polymers and prepolymers of polyethylene, ethylene vinyl acetate, polypropylene, polyesters, polyurethanes and epoxies. Preferably about 0.5 to 50 weight % of wax, polymer or prepolymer (including curing agent) is added to the metal powder. The average particle size of the binder is not particularly critical since it melts in the molding process but to facilitate uniformity in the mixture, particle sizes approximating those of the metal particles are preferred.

The dense and binder powders are dry blended and compressed into a punch and die set at a compression force within the approximate range of 10-40 tons/in$^2$ which should generate enough heat from interparticle friction to melt the binder and permit it to flow into the voids between the other particles.

After being allowed to cool or cure, the resulting product is a matrix of mechanically and adhesively bonded particles. The density of the matrix is dependent upon the force of compression and the ratio of dense material to binder materials.

The strength of the parts manufactured according to this embodiment of the invention can be altered in several ways. If it is desired to increase the strength, greater amounts of binder may be added, thus increasing the particle adhesion aspect of strength. This will tend to decrease the density of the product.

Parts manufactured according to this embodiment are generally more fragile and thus more susceptible to damage, during handling, compared to those made by the sintering method described above. The density element of this embodiment may be coated or encapsulated with polyurethane or other suitable polymer. This can be accomplished by electrostatic powder coating techniques as are commonly used in metal finishing processes. These powder coating techniques permit accurate control of the coating thickness and leave no residual solvents. The preferred polymer for use as a coating is polyurethane, because of its biocompatibility, toughness and strength.

When the same polymer is selected as the binder for use in the metal/binder matrix and also selected as the coating material, the highest adhesive strength of the coating to the underlying matrix is achieved.

EXAMPLE I

Hollow cylindrical samples configured as shown in FIG. 2, O. D. 0.91 in., I. D. 0.2", length 1.33" were formed by compressing 99% wt iron powder (100%<100 mesh, 85%<325 mesh) and 1% petroleum based wax lubricant (Accra Wax) in a suitable die at 30 tons/in$^2$ to achieve a green density of 6.83 gm/ml and a green strength of 1770 psi. The samples were then sintered in an inert atmosphere composed of an endothermic gas made by cracking natural gas with air over a catalyst at 2050° F. for 30 minutes and allowed to cool. The samples possessed a radial crush strength of 2600 pounds which was equivalent to a transverse rupture strength of approximately 18,500 psi. Samples so manufactured were subjected to a fragmentation test by impact with a steel blade having a 1 mm thick edge at a velocity of 2 meters/second. All samples fragmented without damage to the blade which was comparable to blades used in rendering machinery.

EXAMPLE II

A density element configured as described in Example 1 is formed from a uniform mixture of 92% by wt of the iron powder of Example 1 and 8% 100 mesh ethylene vinyl acetate polymer (40% vinyl acetate). The mixture is compressed in a suitable mold at 15 tons/in$^2$ and about 200° F. to produce a density of about 5 gm/ml and a radial crush strength of about 500–1000 pounds. Samples will disintegrate into small fragments without damage to cutting blades when subjected to the fragmentation test described in Example 1.

This invention has described in detail with particular reference to certain preferred embodiments thereof, but it will be understood that variations and modifications can be affected within the spirit and scope of this invention which is limited only by the following claims wherein:

We claim:

1. A density element for use in a ruminal drug delivery device comprising an agglomeration of high density particles bonded together, said density element having:
   a) a density of at least 2.2 gm/ml and sufficient to maintain the delivery device in the rumen of a living animal; and
   b) a transverse rupture strength no greater than about 30,000 psi such that said element fragments upon contact with the blades of grindng equipment without damage to the blades; said density element being free of the drug being delivered and having a corrosion resistance sufficient to prevent any significant loss in weight of said density element in the rumen from insertion to slaughter.

2. The element of claim 1 wherein the density of the element is within the range of 2.2-7.6 gm/ml.

3. The density element of claim 2 wherein the element is formed by:
   a) dry blending particles consisting entirely of iron with from 5-50% by wt of particles of a binder material to form a mixture;
   b) compressing said mixture in a mold at temperatures sufficient to cause said binder material to melt and flow into the voids between said iron particles; and
   c) coating said density element.

4. The density element of claim 3 wherein said binder is selected form the group consisting of waxes, polymers and prepolymers.

5. The density element of claim 3 which further comprises the step of coating said density element with a polymer.

6. The density element of claim 5 wherein the binder material is formed from the same polymer as the coating material.

7. The density element of claim 3 wherein said compressing step utilizes forces within the range of about 10-40 tons/in$^2$.

8. A ruminal drug delivery device comprising, in combination:
   a) a dosage of a drug to be delivered to the rumen of a ruminant animal; and
   b) density element means for maintaining said device in the rumen of said animal, said density element means being separate from said dosage and comprising an agglomeration of high-density particles bonded together, said density element means having (i) a density of at least 2.2 gm/ml and sufficient to maintain the overall density of said delivery device above about 1.5 gm/ml; and (ii) a transverse rupture strength no greater than about 30,000 psi and such that said density element fragments upon contact with moving cutting blades without damage to said blades, said density element means being free of the drug being delivered and having a corrosion resistance sufficient to prevent significant loss of weight in the rumen from administration to slaughter.

9. The delivery device of claim 8 wherein said density element has a density of from about 2.2–7.6 mg/ml.

10. The density element of claim 8 wherein said density element is comprised predominantly of iron.

11. The device of claim 8 wherein said density element is formed by:
   a) dry blending particles consisting entirely of iron with from 5–50% by wt of particles of a binder material to form a mixture;
   b) compressing said mixture in a mold at temperatures sufficient to cause said binder material to melt and flow into the voids between said iron particles; and
   c) coating said density element.

12. The device of claim 11 wherein said binder is selected from the group consisting of waxes, polymers and prepolymers.

13. The device of claim 11 which further comprises the step of coating said density element with a polymer.

14. The device of claim 13 wherein the binder material is formed from the same polymer as the coating material.

15. The device of claim 13 wherein said compressing step utilizes forces within the range of about 10–40 tons/in$^2$.

16. The device of claim 8 further comprising means for displacing said dosage from said device upon exposure of said device to ruminal fluid.

17. The device of claim 16 wherein said means for displacing said dosage comprises a material which expands upon exposure of said device to ruminal fluid.

* * * * *

UNITED STATES PATENT AND TRADEMARK OFFICE
CERTIFICATE OF CORRECTION

PATENT NO. : 5,206,024
DATED : April 27, 1993
INVENTOR(S) : John R. Peery and James B. Eckenhoff It is certified that error appears in the above-identified patent and that said Letters Patent is hereby corrected as shown below:

Claim 1, column 6, line 34, "grindng" should read -- grinding --.

Claim 4, column 6, line 52, "form" should read -- from --.

Signed and Sealed this

Eleventh Day of January, 1994

Attest:

BRUCE LEHMAN

*Attesting Officer*  *Commissioner of Patents and Trademarks*